(12) United States Patent
Hirata et al.

(10) Patent No.: US 8,545,424 B2
(45) Date of Patent: Oct. 1, 2013

(54) HIP SUPPORT MEMBER

(75) Inventors: Takashi Hirata, Wako (JP); Kei Shimada, Wako (JP); Takako Fujii, Kyoto (JP)

(73) Assignee: Honda Motor Co., Ltd., Tokyo (JP)

( * ) Notice: Subject to any disclaimer, the term of this patent is extended or adjusted under 35 U.S.C. 154(b) by 1254 days.

(21) Appl. No.: 11/919,074

(22) PCT Filed: Apr. 24, 2006

(86) PCT No.: PCT/JP2006/308552
§ 371 (c)(1),
(2), (4) Date: Oct. 23, 2007

(87) PCT Pub. No.: WO2006/123516
PCT Pub. Date: Nov. 23, 2006

(65) Prior Publication Data
US 2009/0306564 A1 Dec. 10, 2009

(30) Foreign Application Priority Data
May 17, 2005 (JP) ................................. 2005-143424

(51) Int. Cl.
*A61F 13/00* (2006.01)
(52) U.S. Cl.
USPC .................................. 602/24; 602/19; 602/23
(58) Field of Classification Search
USPC ..................... 602/19, 24, 5, 16, 23; 128/96.1, 128/846, 869, 882, 100.1, 101.1; 601/32–35; 623/26
See application file for complete search history.

(56) References Cited

U.S. PATENT DOCUMENTS

| 6,540,703 | B1 * | 4/2003 | Lerman | 602/5 |
| 7,048,707 | B2 * | 5/2006 | Schwenn et al. | 602/26 |

FOREIGN PATENT DOCUMENTS

| JP | 7-31014 | 6/1995 |
| JP | 08-317947 | 3/1996 |
| JP | 2002-301124 | 10/2002 |
| JP | 2003-220102 | 8/2003 |
| JP | 2005-000634 | 1/2005 |

* cited by examiner

*Primary Examiner* — Kim M Lewis
(74) *Attorney, Agent, or Firm* — Squire Sanders (US) LLP

(57) ABSTRACT

When securing a frame (7) made of a rigid member for carrying a heavy object such as a drive unit (3) for a walking assistance device on the hip of a wearer, a hip protective belt (4) made of fabric is wrapped around the hip of the wearer, and the frame (7) is secured thereon via a flexible plate (5) and a pressure plate (6) located on an outer side of the flexible plate (5) and having a higher rigidity than the flexible plate (5). The intermediate members allow the wearer to feel the rigidity of the frame in a mitigated manner, and the wearer would not experience any discomfort from the pressure of the frame even when the posture of the wearer is changed. The hip protective belt can readily conform to the body contour of the wearer, but the frame would not deform. Because the intermediate members absorb the difference in the builds of different wearers, the frame may come in a small number of different sizes to fit almost any wearer allowing the hip support member can be mass produced at low cost.

8 Claims, 4 Drawing Sheets

HIP SUPPORT MEMBER

TECHNICAL FIELD

The present application claims priority from Japanese application No. 2005-143424 filed May 17, 2005, and the contents of this Japanese patent application are incorporated in the present application by reference.

The present invention relates to a hip support member for enabling a wearer to carry on the hip of the wearer a heavy object such as a walking assistance device for providing an assistance to a person who has a difficulty in walking by himself owing to the lack of muscular force.

BACKGROUND OF THE INVENTION

Various walking assistance devices have been proposed for the purpose of providing an assistance to a person who has a difficulty in walking by himself owing to the lack of muscular force caused by external injuries, diseases and aging, and such a device typically includes a power actuator fitted on the wearer near his hip joint or knee joint to assist the movement of his lower limbs. Conventionally, in such a walking assistance device, it was typical to support an actuator on a lower limb of the wearer with the aid of support members that are secured to the femoral part and crus (lower leg) of the wearer by fastening belts or the likes.

In a walking assistance device, a hip support member is worn on the hip of the wearer typically by passing a belt around the hip. In such a case, it is preferable not only to provide an assisting force for maintaining an upright posture but also to minimize the discomfort to the wearer during use, and a walking assistance device meeting such a need has been proposed (see Japanese patent laid open publication No. 2005-000634, for instance).

When wearing a support member on the hip of a wearer, it is necessary to minimize the load on the hip, and it can be accomplished, for instance, by using an athletic supporter. There is proposed an athletic supporter that straightens the spine by effectively applying a pressure to the back of the wearer without excessively pressing the middle abdomen (see Japanese patent laid open publication No. 08-317947, for instance).

BRIEF SUMMARY OF THE INVENTION

Task to be Accomplished by the Invention

It is highly important for the (exoskeletal) support member of a walking assistance device to be able to fit the body contour of the wearer when worn on the body (hip portion) of the wearer. As a method for achieving a desired fit, it has been practiced in conventional medical support members to use a thermoplastic plastic material and shape it by directly applying it to the body of the user. Thereby, the support member is enabled to closely fit each particular wearer, and the comfort of the wearer can be improved.

However, it is a highly laborious process to shape a support member for each individual wearer, and the cost inevitably rises similarly as the case of a custom made production. Also, when an athletic hip supporter is used, since it is typically provided with a lozenge shaped back portion that broadly covers the hip area, and a plurality of ribs provided in the back portion reduce the flexibility thereof, the wearer tends to experience discomfort owing to the excessive rigidity of the back portion depending on the posture of the wearer.

In view of such problems of the prior art, a primary object of the present invention is to provide a hip support member that reduces the discomfort to the wearer during use while accommodating the differences in the build of different wearers.

Means to Achieve the Task

To achieve such an object, the present invention provides a hip support member for enabling a wearer to wear a frame (7) made of a rigid member for carrying a heavy object, comprising: a hip protective belt (4) having a flexibility that allows the hip protective belt to conform to a body contour of the wearer and wrapped around a hip of the wearer; and an intermediate member (5, 6) interposed between the hip protective belt and frame and having a rigidity intermediate between those of the hip protective belt and frame so as to absorb a difference in deformation between the hip protective belt and frame.

Thus, when using a frame made of a rigid member for carrying a heavy object, by providing an intermediate member between a hip protective belt wrapped around the hip of the wearer and frame, and selecting the rigidity of the intermediate member so as to be intermediate between those of the hip protective belt and frame, the feel of the rigidity of the frame is mitigated by the intermediate member before it is transmitted to the wearer via the hip protective belt, and the wearer would not feel constrained by the frame even when the wearer changes his posture during use. Also, because the frame would not deform while the hip protective belt can readily deform itself so as to conform to the body contour of the wearer, even when a difference (gap) is created between the hip protective belt and frame depending on the build of the particular wearer, this difference can be absorbed by the elastic deformation of the intermediate member, and the frame can accommodate a certain range of the builds of potential wearers. Therefore, when the frame is prepared in three different sizes S, M and L, it can essentially fit most of the population. This helps to reduce the cost of the hip support member by allowing the frame to be prepared as a ready made component as opposed to a custom made frame.

In particular, it is preferable that the intermediate member comprises a flexible body-side plate (5) arranged on an outer side of the body of the wearer and pliant enough to conform to an outer contour of the hip of the wearer and an outer plate (6) arranged on an outer side of the body-side plate and locally engages the body-side plate at a higher rigidity than the body-side plate. These plates may comprise resiliently deformable plate members. Thus, the intermediate member makes the transition in rigidity from the frame to the hip protective belt into a gradual one and the pressure from the frame is transmitted to the body-side plate via the outer plate so that the pressure from the rigid frame is prevented from being directly applied to the body of the wearer.

In view of the cross sectional shape and anatomy of the hip of a wearer, the outer plate (6) may comprise two sections that are located between the body-side plate (5) and frame on either side of a spine of the wearer, and each section comprises a middle part pivotally supported by the frame and two ends that curve away from the frame and engage the body-side plate. For similar reasons, the hip protective belt may be provided with a plurality of layers, the layers being largest in number at a part thereof corresponding to the back of the wearer and being progressively reduced in number toward each side end. Thereby, the central part of the hip protective belt is allowed to oppose the recess in the center of the back, and this enhances the stability of the hip protective belt when worn by a wearer.

To prevent the heavy object carried by the frame from being directly engaging the body of the wearer, the hip support member may be integrally provided with a protective pad (13) which is to be interposed between the heavy object carried by the frame and the body of the wearer. To impart an adequate flexible to the hip protective belt which is most directly applied to the body of the wearer, the hip protective belt may be essentially made of fabric or non-woven fabric. To finally secure the hip support member around the hip of the wearer, the hip support member may further comprise a fastening belt (14) that extends from one end of the frame to the other along an outer peripheral surface of the hip protective belt around the hip of the wearer.

BRIEF DESCRIPTION OF THE DRAWINGS

Now the present invention is described in the following with reference to the appended drawings, in which.

DETAILED DESCRIPTION OF THE PREFERRED EMBODIMENTS

Figure 1:
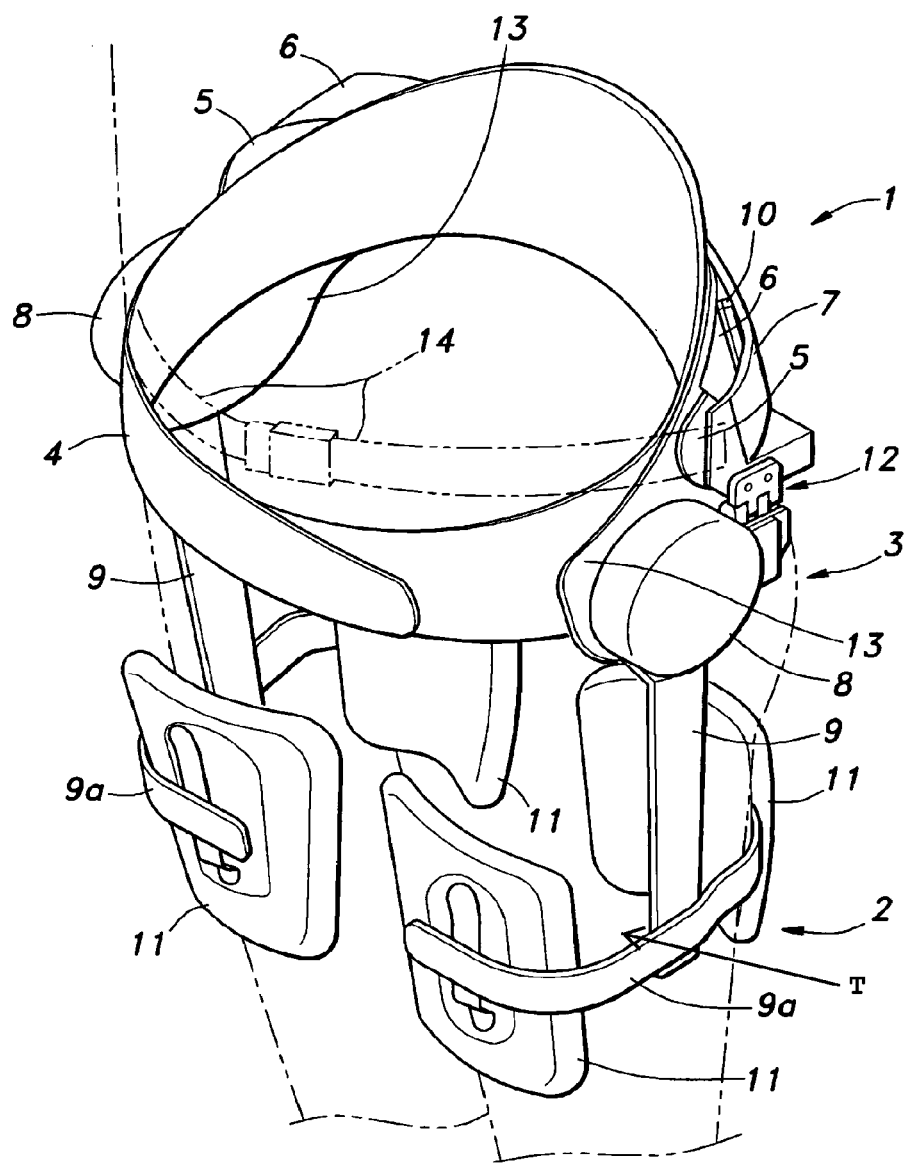
FIG. 1 is a perspective view showing an overall structure of a walking assistance device embodying the present invention.

FIG. 1 is a simplified structural view of a walking assistance device embodying the present invention as worn on the body of a wearer (indicated by the double-dot chain-dot line). This walking assistance device comprises a hip support member 1, a pair of femoral support members 2 and a pair of drive units 3 for producing an assist power. By wearing the hip support member 1 on the hip of the wearer and each femoral support member 2 on the corresponding femoral region T of the wearer, the torque produced by the drive unit 3, which is supported by the hip support member 1 and connecting the two support members 1 and 2 to each other, is transmitted to the femoral region T of the wearer so that an assist force that would compensate for the reduced muscle power of the wearer is given to the wearer.

Figure 2:
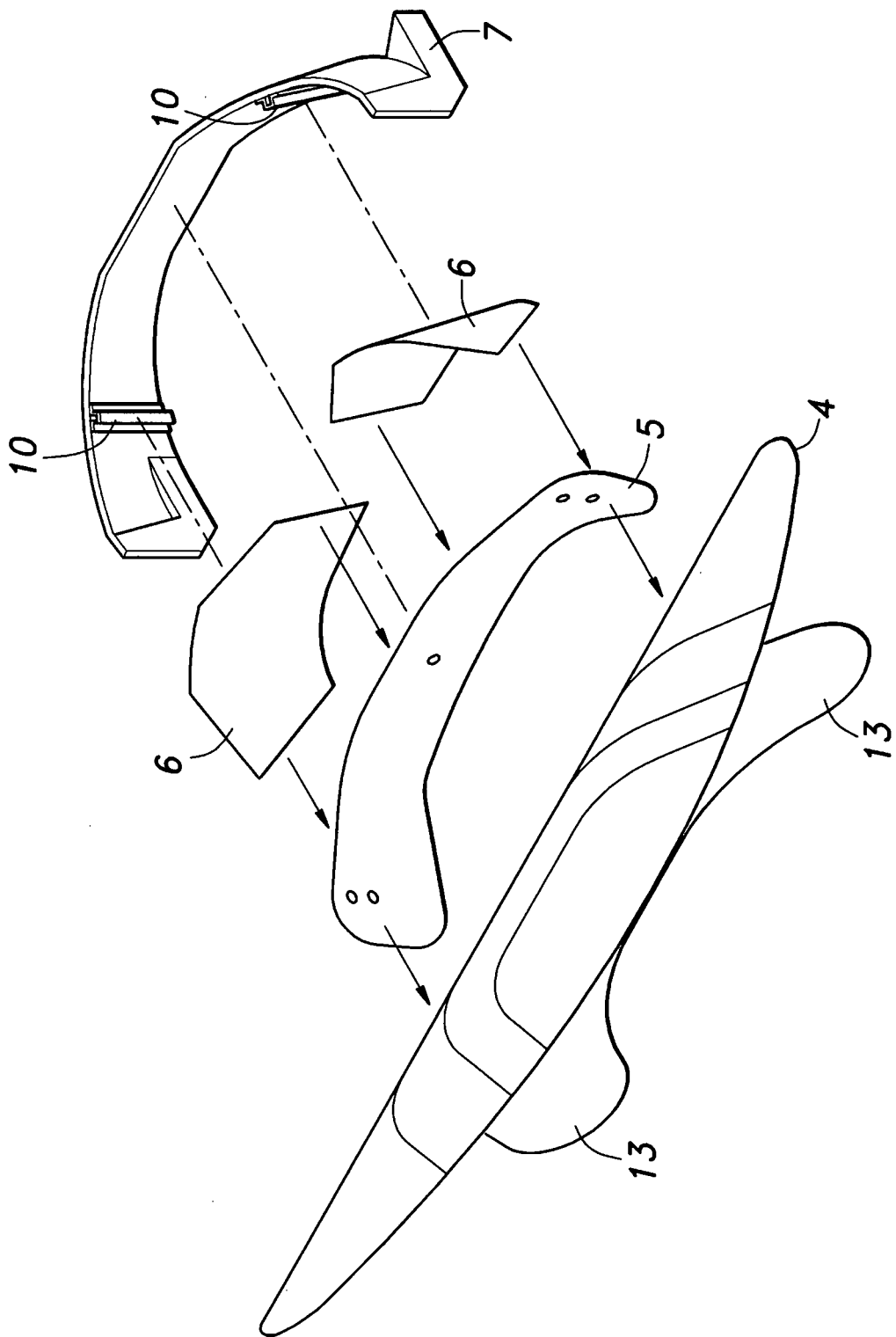
FIG. 2 is an exploded perspective view of the hip support member.

As also shown in FIG. 2, the hip support member 1 comprises a hip protective belt 4 made of fabric, for instance, and wrapped around the hip of the wearer, a flexible plate (body-side plate) 5 arranged on an outer side of the hip protective belt 4, a pair of pressure plates (outer plate) 6 arranged on laterally mutually spaced areas on an outer side of the flexible plate 5 and a frame 7 arranged on an outer side of the pressure plates 6. The flexible plate 5 and pressure plates 6 jointly form an intermediate member.

Figure 3:
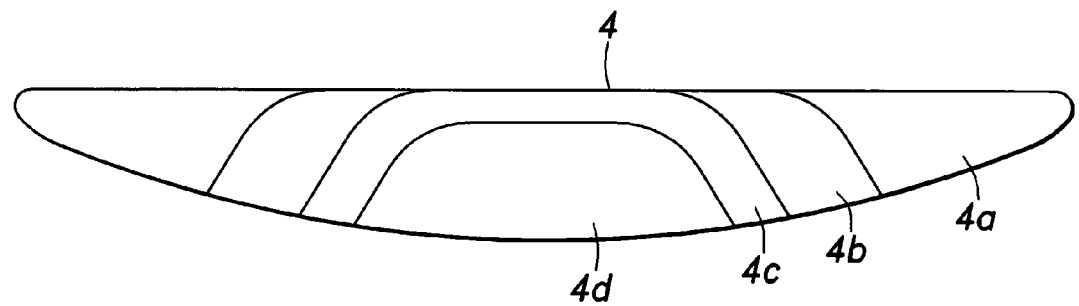
FIG. 3 is a plan view of the hip support member.

The hip protective belt 4 is provided with a plurality of layers, the layers being greatest in thickness at a lengthwise middle part thereof and being progressively reduced in thickness toward each end. For instance, as shown in FIG. 3, the hip protective belt 4 may be formed by laying an elongated section 4a extending over the entire length of the hip protective belt 4, a medium length section 4b, a short section 4c and a back section 4d engaging the back of the hip of the wearer by a certain width, all made of a fabric consisting of a same material and having a same thickness, one over another in a laterally symmetric fashion. Thereby, the hip protective belt 4 is allowed to conform to the recessed shape of the back of the hip of the wearer, and the hip protective belt 4 can be worn on the hip of the wearer in a stable fashion. The two ends of the hip protective belt 4 are provided with a surface fastener so that the wrapping length of the hip protective belt 4 may be adjusted depending on the size of the hip of the wearer.

The flexible plate 5 consists of a molded plastic member, for instance, and is higher in rigidity than the hip protective belt 4 made of fabric but is pliant or flexible enough to be wrapped around the hip of the wearer. In the illustrated embodiment, the flexible plate 5 is provided with an arcuate shape and dimensioned so as to surround the back and sides of the hip of the wearer. The flexible plate 5 is joined to the frame 7 by connecting a lengthwise middle part of the flexible plate 5 to a middle part of the frame 7 by using a pin or the like.

Each pressure plate 6 may consist of a molded plastic member having a higher rigidity than the flexible plate 5, and is provided with a shape of an elongated dish so as to cover the base end of the corresponding femoral portion of the wearer. To the part of the inner surface of the frame 7 opposing the base end of each femoral portion of the wearer is attached a resilient support member 10 made of a spring member, and this resilient support member 10 is connected to a central part of the corresponding pressure plate 6. Each resilient support member 10 is adapted to flex with respect to the lengthwise line (the circumferential line of the hip) so that each pressure plate 6 is allowed to flex in the manner of a seesaw with respect to the inner circumferential surface of the frame 7. It is also possible to use a normal hinge using a hinge pin instead of an elastic hinge such as the resilient support member 10.

The frame 7 may consist of a metallic material and have a higher rigidity than the pressure plates 6. The frame 7 is provided with an arcuate shape so as to surround the back and two sides of the hip of the wearer, and is dimensioned so as to receive the hip protective belt 4, flexible plate 5 and pressure plates 6 therein. In particular, the frame 7 may be configured to partly surround the hip of the wearer in such a manner as to accommodate variations in the size of the hip of each particular wearer.

Each drive unit 3 comprises an actuator 8 integrally supported by the frame 5 on the corresponding side of the hip, an arm 9 that is actuated by the corresponding actuator and extending along the outer side of the corresponding femoral portion and a femoral pad 11 supported by an arm extension 9a extending in the fore-and-aft direction from the lower end of the arm 9. As shown in FIG. 1, front and rear ends of the arm extension 9a of the arm 9 are each fitted with a femoral pad 11 so as to engage the front and rear sides of the femoral portion.

Each actuator receives a supply of electric power from a battery not shown in the drawings. When a leg is moved in either forward or rearward direction, such a movement is transmitted to the actuator 8 via the arm 9 and is detected by a sensor incorporated in the actuator 8. According to the detected movement of the leg, the electric motor in the actuator 8 is turned in such a manner that the resulting output torque of the electric motor is transmitted to the femoral portion of the leg via the arm 9 and assists the movement of the leg.

Each actuator 8 is supported on the corresponding side end of the frame 7 via a hinge 12. The tilting movement of the actuator 8 that is permitted by the hinge 12 is effected in a lateral direction. Therefore, even when the position of each femoral pad 11 engaging the femoral portion of the wearer shifts laterally owing to the variations in the build of the wearer, it can be accommodated by the lateral tilting movement of the arm 9. Also, to prevent each actuator 8 from directly engaging a side of the corresponding femoral portion, a protective pad 13 is integrally attached to the hip protective belt 4.

Figure 4:
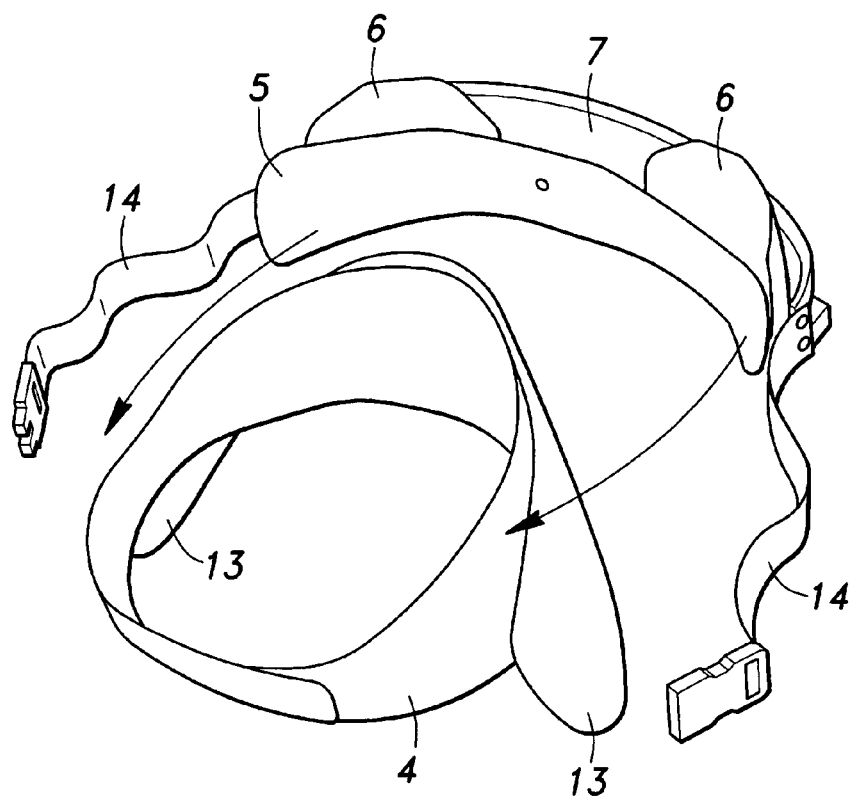
FIG. 4 is a perspective view showing the mode of wearing the hip support member on a wearer.

As shown in FIG. 4, a fastening belt 14 is secured to each lateral end of the frame 7 so that the frame 7 may be secured around the hip of the wearer by joining the opposing ends of the fastening belts 14 with a buckle. The length of the belts 14 can be adjusted so as to accommodate the variations in the size of the wearer and selecting a desired fastening force. The flexible plate 5 and pressure plates 6 are attached to the frame 7 so that the frame assembly may be handled separately from the hip protective belt 4. Therefore, when wearing the hip support member 1, first, the hip protective belt 4 is wrapped around the hip of the wearer, and then with the flexible plate 5 applied to the back and two sides of the hip protective belt 4, the frame 7 is secured around the hip of the wearer.

The actuators 8 that are carried by the frame 7 each have a significant weight as it includes an electric motor and other components (which may include a battery not shown in the drawings). Therefore, for the frame 7 to be able to carry such heavy actuators, the frame 7 is required to have an adequate rigidity. Therefore, the frame 7 is not compliant to the body of the wearer, and could cause discomfort to the wearer by applying a pressure thereto when the wearer changes his posture.

Figure 5:
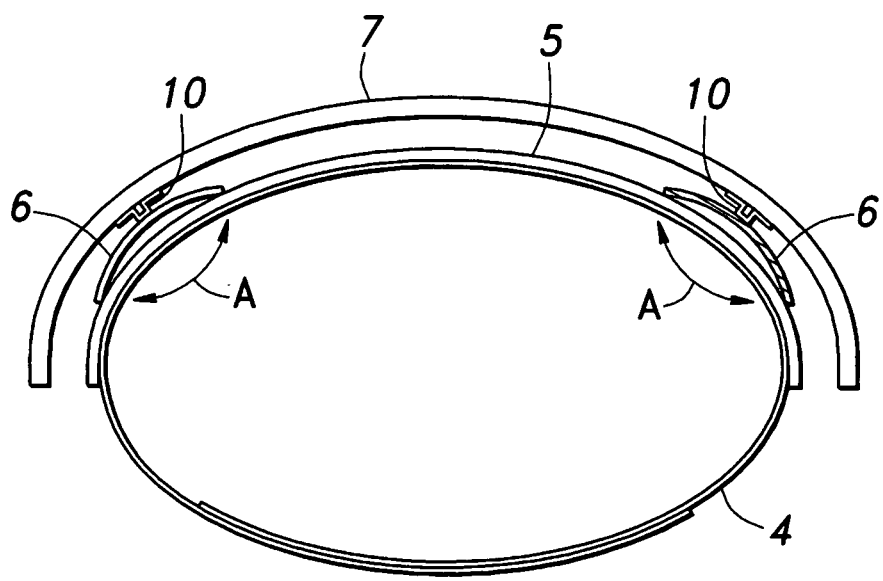
FIG. 5 is a plan view showing the mode of wearing the hip support member.

As shown in FIG. 5 also, the hip support member 1 of the present invention thus comprises the hip protective belt 4, flexible plate 5, pressure plates 6 and frame 7 in that order as seen from the side of the body of the wearer, and the hip protective belt 4 adjacent to the hip of the wearer is the softest, the remaining components being given with a progressively higher rigidity from inside to outside. Therefore, the hip protective belt 4 can be made of pliant material such as fabric so as to be wrapped around the hip of the wearer, and can accommodate wearers of a wide range of build. Because the hip protective belt 4 is surrounded by the flexible plate 5 having a higher rigidity than the hip protective belt 4 and the flexible plate 5 is attached to the inner side of the frame 7 via the pressure plates 6 having a higher rigidity than the flexible plate 5, the differences in shape between the hip protective belt 4 conforming to the body contour of the wearer and the frame 7 having a high rigidity can be absorbed by these plates 5 and 6, and the wearer is prevented from directly feeling the high rigidity of the frame 7 owing to the existence of the intervening plates 5 and 6.

The part of the hip support member 1 that directly engages the body of the wearer is the hip protective belt 4 which is wrapped around the hip of the wearer. Because the hip protective belt 4 is made of pliant material such as fabric, the wearer would not experience any discomfort even when he changes his posture. The hip protective belt 4 is surrounded by the flexible plate 5 over a range that corresponds to the back of the wearer. The flexible plate 5 has a higher rigidity than the hip protective belt 4 made of fabric, but is made of such material as to still enable the flexible plate 5 to conform to the contour of the hip of the wearer and accommodate changes in the posture of the wearer. In other words, the flexible plate 5 is not so rigid as to prevent deformation as required, and would not cause discomfort to the wearer even when he changes his posture.

On the other hand, the frame 7 has such a high rigidity as not to follow changes in the posture of the wearer, but the pressure plates 6 resiliently supported by the frame 7 engage the flexible plate 5. Therefore, the frame 7 would not engage the entire area of the flexible plate 5. Because each pressure plate 6 is supported by the fame 7 via the resilient support member 10 so as to be tiltable along the inner circumferential surface of the frame 7 as indicated by arrow A in FIG. 5, even when the outer contour of the flexible plate 5 changes depending on the build of each particular wearer, the two ends of each pressure plate 6 (the two ends of the arcuate shape shown in FIG. 5) can evenly engage the flexible plate, and this helps the hip support member 1 accommodate the different builds of different wearers.

Each pressure plate 6 only locally engages the flexible plate 5, but the resulting pressure is evenly distributed to the hip protective belt 4 by the flexible plate 5. Therefore, the wearer would not feel the rigidity of the frame 7 as a localized pressure, and is thereby prevented from experiencing discomfort from the rigid frame 7 even when the posture of the wearer is changed.

It may not be possible to fit the frame 7 to every wearer, but the frame 7 can accommodate a large range of differences in the build of the wearer if it comes with a small number of different sizes such as S, M and L. Therefore, the frame can be mass produced so that the manufacturing cost can be reduced as compared with the conventional frame which is custom made for the build of each particular wearer by molding thermoplastic resin material against the actual wearer.

INDUSTRIAL APPLICABILITY

The hip support member of the present invention is adapted to favorably support a frame made of a rigid material so as to carry a heavy object, and can accommodate different builds of different wearers. The hip support member of the present invention is useful not only as a support member for a walking assistance device but also as a support member for supporting a rigid frame for other purposes.

GLOSSARY

| | | | |
|---|---|---|---|
| 1 | hip support member | 4 | hip protective belt |
| 4a, 4b, 4c, 4d | fabric sections (layered structure) | | |
| 5 | flexible plate (body-side plate) | 6 | pressure plate (outer plate) |
| 7 | frame | | |
| 10 | resilient support member (absorbing means based on resilient deformation) | | |
| 13 | protective pad | | |

The invention claimed is:

1. A hip support member, comprising:
   a frame made of a rigid member for carrying a heavy object and configured to be worn by a wearer;
   a hip protective belt having a flexibility that allows the hip protective belt to conform to a body contour of the wearer, and configured to be wrapped around a hip of the wearer; and
   an intermediate member interposed between the hip protective belt and the frame and having a rigidity intermediate between those of the hip protective belt and the frame so as to absorb a difference in deformation between the hip protective belt and the frame, wherein the hip protective belt is surrounded by the intermediate member over a range that corresponds to a back of the wearer, and wherein the intermediate member comprises a flexible body-side plate configured to be located on an outer side of a body of the wearer and pliant enough to conform to an outer contour of the hip of the wearer and an outer plate arranged on an outer side of the flexible body-side plate and configured to locally engage the flexible body-side plate at a higher rigidity than the flexible body-side plate.

2. A hip support member according to claim 1, wherein the outer plate comprises two sections that are located between the flexible body-side plate and the frame, and that are configured to be located on either side of a spine of the wearer, and each section comprises a middle part pivotally supported by the frame and two ends that curve away from the frame and engage the flexible body-side plate.

3. A hip support member according to claim 1, wherein the hip protective belt is essentially made of fabric or non-woven fabric.

4. A hip support member according to claim 1, wherein the outer plate and the flexible body-side plate comprise resiliently deformable plate members.

5. A hip support member, comprising:
a frame made of a rigid member for carrying a heavy object and configured to be worn by a wearer;
a hip protective belt having a flexibility that allows the hip protective belt to conform to a body contour of the wearer, and configured to be wrapped around a hip of the wearer; and
an intermediate member interposed between the hip protective belt and the frame and having a rigidity intermediate between those of the hip protective belt and the frame so as to absorb a difference in deformation between the hip protective belt and the frame,
wherein the hip protective belt is surrounded by the intermediate member over a range that corresponds to a back of the wearer, and
wherein the hip support member is integrally provided with a protective pad which is configured to be interposed between a heavy object carried by the frame and a body of the wearer.

6. A hip support member, comprising:
a frame made of a rigid member for carrying a heavy object and configured to be worn by a wearer;
a hip protective belt having a flexibility that allows the hip protective belt to conform to a body contour of the wearer, and configured to be wrapped around a hip of the wearer; and
an intermediate member interposed between the hip protective belt and the frame and having a rigidity intermediate between those of the hip protective belt and the frame so as to absorb a difference in deformation between the hip protective belt and the frame,
wherein the hip protective belt is surrounded by the intermediate member over a range that corresponds to a back of the wearer, and
wherein the hip protective belt is provided with a plurality of layers, the plurality of layers being largest in number at a part thereof corresponding to the back of the wearer and being progressively reduced in number toward each side end.

7. A hip support member according to claim 6, wherein the hip protective belt is essentially made of fabric or non-woven fabric.

8. A hip support member, comprising:
a frame made of a rigid member for carrying a heavy object and configured to be worn by a wearer;
a hip protective belt having a flexibility that allows the hip protective belt to conform to a body contour of the wearer, and configured to be wrapped around a hip of the wearer;
an intermediate member interposed between the hip protective belt and the frame and having a rigidity intermediate between those of the hip protective belt and the frame so as to absorb a difference in deformation between the hip protective belt and the frame,
wherein the hip protective belt is surrounded by the intermediate member over a range that corresponds to a back of the wearer; and
a fastening belt that extends from one end of the frame to another end along an outer peripheral surface of the hip protective belt, and that is configured to extend around the hip of the wearer.

\* \* \* \* \*